US011207326B2

United States Patent
Cohen et al.

(10) Patent No.: US 11,207,326 B2
(45) Date of Patent: Dec. 28, 2021

(54) ACCELERATED TREATMENT OF COVID-19 AND SAR'S TYPE VIRUSES

(71) Applicants: Binyomin A. Cohen, Brooklyn, NY (US); Monicka C. Jones, Brooklyn, NY (US)

(72) Inventors: Binyomin A. Cohen, Brooklyn, NY (US); Monicka C. Jones, Brooklyn, NY (US)

( * ) Notice: Subject to any disclaimer, the term of this patent is extended or adjusted under 35 U.S.C. 154(b) by 0 days.

(21) Appl. No.: 16/883,115

(22) Filed: May 26, 2020

(65) Prior Publication Data

US 2021/0369719 A1 Dec. 2, 2021

(51) Int. Cl.
| | | |
|---|---|---|
| A61K 31/522 | (2006.01) | |
| A61K 9/19 | (2006.01) | |
| A61K 9/00 | (2006.01) | |
| A61P 31/14 | (2006.01) | |

(52) U.S. Cl.
CPC .......... *A61K 31/522* (2013.01); *A61K 9/0019* (2013.01); *A61K 9/0073* (2013.01); *A61P 31/14* (2018.01)

(58) Field of Classification Search
CPC .. A61K 31/522; A61K 9/0073; A61K 9/0019; A61P 31/14
USPC ................................................ 514/45; 435/5
See application file for complete search history.

(56) References Cited

U.S. PATENT DOCUMENTS 10,300,226 B2    5/2019   Cohen

FOREIGN PATENT DOCUMENTS

WO    WO 2015/063239    *    5/2015

OTHER PUBLICATIONS

The Engineering Toolbox: Air-Composition and Molecular Weight, 2003, pp. 1-7.*
Han et al, Ann Am Thorac Soc, 2015, 12(5), 765-774.*
Mason, Eur Respir J., Apr. 9, 2020, pp. 1-5.*
Shintake T. Possibility of Disinfection of SARS-CoV-2 (COVID-19) in Human Respiratory Tract by Controlled Ethanol Vapor Inhalation. https://arxiv.org/ftp/arxiv/papers/2003/2003.12444.pdf (Mar. 13, 2020) (Year: 2020).*
Mason RJ. Pathogenesis of COVID-19 from a cell biology perspective. Eur Respir J 2020; 55: 2000607 [https://doi.org/10.1183/13993003.00607-2020].
Choi, O. H et al., Caffeine and theophylline analgogues: correlation of behavioral effects with activity as adenosine receptor antagonists and as phosphodiesterase inhibitors, Life Sciences, vol. 43, pp. 367-398, 1988.
A Clinical Trial of Nebulized Surfactant for the Treatment of Moderate to Severe COVID-19 (COVSurf), University Hospital Southampton NHS Foundation Trust, ClinicalTrials.gov Identifier: NCT04362059, first posted Apr. 24, 2020, last update posted May 28, 2020.
New Treatment for COVID-19 Using Ethanol Vapor Inhalation, Mansoura University, ClinicalTrials.gov Identifier: NCT04554433, first posted Sep. 18, 2020, last update posted Oct. 28, 2020.
Mirastschijski, Ursula, et. al., Lung Surfactant for Pulmonary Barrier Restoration in Patients With COVID-19 Pneumonia, Fron Med (Lausanne), May 22, 2020, doi:10.3389/fmed.2020.00254.
Piva, Simone, et al., Surfactant therapy for COVID-19 related ARDS: a retrospective case-control pilot study, Respir. Res. 2021; 22:20; published online Jan. 18, 2021; doi: 10.1186/s12931-020-01603-w.
Suwabe, A., et al., Artificial surfactant (Surfactant TA) modulates adherence and superoxide production of neutrophils, Am J Respir Crit Care Med. Dec. 1998; 158(6):1890-9 (Abstract Only).
Mandile, Olivia, Neonatal Respiratory Distress Syndrome and Its Treatment with Artificial Surfactant, The Embryo Project Encyclopedia (https://embryo.asu.edu) Aug. 30, 2017; last visited Aug. 6, 2021.
Bassler, Dirk, et al., Proposal for the inclusion of surfactant in the WHO model list of essential medicines, Second Meeting of the Subcommittee of the Expert Committee on the Selection and Use of Essential Medicines, Geneva, Sep. 29 to Oct. 3, 2008.
Avdeev, Surgey, et al., Beneficial effects of inhaled surfactant in patients with COVID-19-associated acute respiratory distress syndrome, Respiratory Medicine 185 (2021)106489.
Surfactant-BL in Adult Acute Respiratory Distress Syndrome Due to COVID-19, Clinical Trial Identifier NCT04568018, first posted Sep. 29, 2020, https://clinicaltrials.gov/ct2/show/NCT045680?term=NCT04568018&draw=2&rank=1, last visited Aug. 7, 2021.
Exogenous Surfactant Through Nebulizer Mask on Clinical Outcomes in Covid-19 Patients (CovidSurf), Clinical Trial Identifier NCT04847375, first posted Apr. 19, 2021; https://clinicaltrials.gov/ct2/show/NCT04847375?term=NCT04847375&draw=2&rank=1, last visited Aug. 7, 2021.
Heistan, Matt, The Main Types of IV Fluids, Aug. 28, 2019, https://www.azivmedics.com/iv-fluids; last visited Aug. 3, 2021.
Ball, Winona Suzanne, IV Fluids (Intravenous Fluids): The 4 Most Common Types; https://nurse.plus/becme-a-nurse/4-most-commonly-used-iv-fluids/; last visited Aug. 3, 2021.
Luisada Aldo A., et al., Alcohol Vapor by Inhalation in the Treatment of Acute Pulmonary Edema, Circulation, vol. V, Mar. 1952, pp. 363-369.

(Continued)

*Primary Examiner* — Yih-Horng Shiao
(74) *Attorney, Agent, or Firm* — Pokalsky Wilczynski Brozek, LLP

(57) ABSTRACT

The present invention provides a solution mixture of 1.8 to 3.7% hypertonic saline, 70 to 85% ethanol as solvent alternating with 10 milliliters 50 to 90% of 75 to 110 mg theobromine in a nebulized aerosol for inhalation by COVID-19 and SARS patients. Alternatively, theobromine may be infused alternating with inhaled nebulized exogenous pulmonary surfactant as replacement. For advanced COVID-19, SARS patients, the inhalation described above may be alternated with an intravenous solution of 1.8% to 2.2% hypertonic solution of theobromine as 450 mg to 650 mg in ethanol, twice daily.

6 Claims, No Drawings

(56) References Cited

OTHER PUBLICATIONS

Manning, Thomas J., Should ethanol be considered a treatment for COVID-19?, Rev Assoc Med Bras 2020; 66 (9):1169-1171.
New Treatment for COVID-19 Using Ethanol Vapor Inhalation, Clinical Trial Identifier NCT04554433, Sep. 18, 2020; https://clinicaltrials.gov/ct2/show/NCT04554433?term=NCT04554433&draw=2&rank=1; last visited Aug. 26, 2021.

* cited by examiner

ACCELERATED TREATMENT OF COVID-19 AND SAR'S TYPE VIRUSES

BACKGROUND OF THE INVENTION

Coronavirus COVID-19 is eliminated on surfaces upon contact with ethanol 70% or higher and in as short a time as under 45 seconds. It is a main thrust of this present invention to provide safe inhalation of aerosolized ethanol alcohol at 70 to 85% as solvent to hypertonic saline that would provide protection against rapid colonization of Covid-19, decreasing the viral load. As such, the safe inhalation would also provide a first line of prophylaxis to those with high exposure and/or in contact with those carrying said virus, such as hospital staff. Safe inhalation would also prove helpful in close quarters with those who are asymptomatic yet are still infected as seen in young children and early teens. Clinics could be set up in short time to provide such aerosolization to such patients. Alternatively, a hand-held nebulizer using ethanol at 70-85% may be used.

DETAILED DESCRIPTION OF THE INVENTION

The present invention provides a mixture/solution used specifically for the COVID-19 and SARs viral infectious disease that impacts and initially gains entry via the airway route. Any nebulizer cup of any medical nebulizer may be used the generate the mixture/solution for inhalation. However, those that generate greater density of smaller aerosol particles, meaning aerosol particles nebulized being sizes below 3 microns with a carrier stream of oxygen-rich air density below 1.30 to 1.28 g/liter would be optimal. Gaseous mixtures as in oxygen, air, along with specific helium dilutions as seen in and applied in U.S. Pat. No. 10,300,226 B2, for example at 25% oxygen mixed with 30% helium as "25% $O_2$: 30% He" would effect a gaseous mixture density of $$(0.30 \times 4)+(0.25 \times 32)+(0.45 \times 28)/22.4=1.2+8+12.6=21.8/22.4=0.973 \text{ g/l}. \quad [a]$$

a. [Density of Compound by Mass and Molar Fraction Each Gas]
This lower gas mixture density powering the nebulizer, would enhance depth of penetration in the airways, conceptually to the level of the terminal bronchioles, and thereby active diffusion into the alveolar clusters to combat the viral damages at that level of the airways.

As an inhaled aerosol of the mixture/solution being the first embodiment of the present invention, the fluid conceived for nebulization is hypertonic saline at 1.8 to 3.7% in a volume of 10 milliliters ("ml") of 50 to 90% Theobromine, said solution mixture itself all dissolved in 5 to 10 ml of 70 to 85% ethanol as solvent. This first and main embodiment of the present invention-this-fluid-is a high percentage of ethanol solution having hypertonic salt and theobromine to decrease the irritation of the inhaled aerosol to the patient and will achieve several goals.

Theobromine is added to cytoprotect the pulmonary type 2 cells since surfactant is damaged by the COVID-19 and SARS viral material, causing lung compliance problems, requiring greater opening pressures thereby making breathing spontaneously harder. Equally, theobromine inhibits phosphodiesterase enzymes that degrade the second messenger cAMP, which regulates intracellular calcium and antagonism of adenosine receptors. Choi O. H., Shamim M. T., Padgett W. L., Daly J. W. (1988). "Caffeine and theophylline analogues, Adenosine receptor antagonist and as phosphodiesterase inhibitors," Life Sci 43, 387-398.

As such, theobromine in the mixture/solution would allow a reduction of a progressive alveolar capillary blocking syndrome sadly common in respiratory distress syndromes and also seen in "Hyaline membrane disease." Equally, greater penetration of the aerosolized particles below 3 microns in diameter of the stated mixture solution of hypertonic salt dissolved in theobromine and ethanol tends to travel farther into the deeper recess of the airways in the lung, by two main principals; first, the nebulized particles being smaller than 3 microns and secondly, the lower carrier gas mixture's density each allow for farther travel into the depth of the airways. Equally, the evaporated hypertonic saline in ethanol is aerosolized as smaller particles achieving a greater travel per tidal volume of air inhaled. Second, the evaporated ethanol exists as vaporized hypertonic salt impacting the airways by reducing coughing. By just usage of either hypertonic salt and/or ethanol individually, either would elicit irritation as coughing activity that would prohibit depth and increased deposition of the nebulized hypertonic ethanol from achieving its goals of depth of penetration and spread within the airways. In addition, allowing greater diminishing of particle size of the aerosol allows greater deposits of aerosolized ethanol at each branched airway sub-division within the airways. Along with the 10 milliliters, 50 to 90% Theobromine in 5 to 10 additional milliliters of ethanol is mixed with hypertonic saline as solvent solution. Both ethanol and NaCl are designed to deconstruct the viral load and inhibit further colonization and hopefully, if applied early enough, prevent any colonization. Alternating the hypertonic saline in solution with ethanol is usage of theobromine as added diluent. Theobromine, "a purine" was added for several reasons; first, to increase the surfactant production of the lungs from cytoprotective pneumocyte type 2 cells by allowing surfactant production or increasing its effects while easing the work of breathing and decreasing the damaging effect of less oxygen diffusion by the SARS and or COVID-19 viral particles colonizing within the lung fields.

An additional and second embodiment of the present invention given with or separate from nebulized inhalation of the mixture/solution is an alternating IV solution for advancing debilitating patients of COVID-19 and or SARS. As the rate of infection time is inconclusive in these viral infectious diseases, theobromine may also be used alternatively via I. V. infusion of a range from 450 mg to 650 mg over a twice daily period to further increase surfactant production in those who have dyspnea and patient reflected $O_2$ saturations below 89% to 91% oxygen saturation. Addition of pulmonary surfactant by this route, via nebulization has immediate benefits, as lung surfactant makes it easier for oxygen to penetrate the lung surface lining and move into the blood. Without the lung surfactant it would be extremely hard to breathe, and transfer of oxygen through the surface that lines the lungs would be very difficult. Normally surfactant is produced by the fetus prior to birth, setting the stage for lungs to breathe properly. In premature newborns, lung surfactant is given as needed replacement since "respiratory distress syndrome" often occurs without it being replaced. This is where breathing is labored and oxygen diffusion is hampered, similar to COVID-19.

It is these inventors' research, as seen in surface deconstruction and destruction of this coronavirus "COVID-19" contacting surfaces, where upon contact with ethanol 70% or higher percentages and hypertonic saline the 'COVID-19' virus is eliminated upon contact, as seen in surface deconstruction and destruction of this cornaviruses "COVID-19. As seen when ethanol contacts surface viral material, this occurs in as short a time postulated as under 45 seconds.

The inhalation of the nebulized chosen mixture solution once given has to have a one to two-hour delay before first giving the nebulized surfactant, this as the mixture solution would damage the given surfactant replacement as stated above. The addition of the venous i.v. mixture solution and surfactant replacement is also conceptually used for individuals more symptomatic.

$$C_{12}H_{22}O_{11} + H_2O \xrightarrow{maltase} 2C_6H_{12}O_6$$
maltose glucose $$C_6H_{12}O_6 \xrightarrow{zymase} 2CH_3CH_2OH + 2CO_2 + 26 \text{ kilocalories}$$
glucose ethanol Fermentation typically yields a solution only about 12-15 percent alcohol because higher concentrations are toxic to the yeast cells used to ferment.

Usage of ethanol alcohol 70 to 85 percent via techniques to aerosolize this organic alcohol for inhalation safely combats the spread of the current COVID-19 pandemic by deconstructing the viral load and preventing and inhibiting colonization of said viral material. Coronavirus is unique in the fact that it has spikes above, that surround its bulk RNA composition. It is postulated that each spike provides protection against foreign (foreign to this virus), drugs and antiviral chemicals designed to inhibit, deconstruct or destroy these viruses conceptualized as COVID-19 and Co-SAR bulk structure. The hypertonicity of the solution 1.8 to 3.7% NaCl as solute will, it is conceptualized, destroy the whole carrier structure of the virus by deconstructing the spike protein by directly denaturing its protein coat(ing). So far as knowledge has been gained in this COVID-19 structure, it is postulated that cell transmission is achieved post entry by the viral coronal having spikes invaginating into the hosts cell membrane and securing an attachment that allows entry within the host cell, conscripting its internal machinery to reproduce its structures. The focus is that the salt herein NaCl within the ethanol will not completely dissolve but will stay suspended within the carrier stream but would slightly dissociate becoming cations and anions and would deconstruct the viral material upon contact. Equally, NaCl as the dissociated salt wet with ethanol would adhere and contact the viral material within the airways; the predominate route of entrance of these viruses. As such, Sodium chloride (NaCl) is soluble in water (360 g/l) while only sparingly soluble in ethanol (0.65 g/l, likely NaCl would dissolve more easily in water but would not dissolve to any appreciable extent in ethanol.

Nebulized Impact on COVID-19

As such, the viral spike(s) will post entry into the airways first, attach and invaginate into a host cell over the first two days, transferring the viral material into the host to invade and mass produce-via replication. It is destructive to the host's biochemical cellular machinery, which elicits a cytokine cascade that may well destroy the host's organs and/or elicit a cytokine storm that is the cause of much morbidly and mortality in the critically ill patients having succumbed to the virus load and immunity response to such load. The main transmission of this virus is known to be via inhalation and contact to the oral nasopharyngeal region as initial route and down further into the airways accessing the lungs of its host. Upon contact and implantation, the virus then colonizes and grows in a short period to increase its viral load to the host, causing biochemical cascades of protective mechanism to protect the host, which sadly end up causing greater damage then assistance.

The benefit of the inhaled ethanol is several fold. First, it is known that ethanol, even isotonic ethanol, tends to inhibits superoxide anion; while this has benefit in and of itself, it is not the primary benefit. What is the main benefit is gross inhibition of viral load and colonization achieved via the ethanol's also causing cell expansion, this by ethanol being an isotonic media. Ethanol functions as hypertonic to the cell, causing expansion and rupture as the hypertonic salt, being 2× that of physiological saline. As such should the viral load via its spikes invaginate the host cells within the airway, such cells intra-airway are initially; it is hypothesized to be first, to engorge the cell with fluid then to extend the cell membranes barriers then burst, ruptured by the ethanol and hypertonic salt inhaled and deposited within the airway. Additionally, in later COVID-19, SARs progression states—in patients who have had the virus already colonized, the usage of intravenous solution conceptually would affect the same damage to the virus even though already fully colonized in the blood and cell stream. Since ethanol is less dielectric than water, together as solution, usage of the hypertonic saline will promote ionic bonding between the sodium ion and the $PO^{3-}$ from the DNA backbone causing extraction of those cells already conscripted by COVID-19 causing disruption and decay of the conscripted viral host cells. This reverses the time sequence of the viral load, allowing more destruction of the viral load even post merging with the host's cells. Without this method of attack upon the COVID-19 disease, the conscription and merging will be unchallenged, typically causing infiltration and inflammation to the lung and its delicate alveolar-capillary membrane with combined resulting pneumonias and oxygen diffusion blockades. This leads to increasing hypoxia; low oxygen levels in blood, and cardiac, kidney, and brain complications requiring supplemental oxygen, and if unchallenged quickly, sadly leading to respiratory failure requiring ventilatory support to prolong life and limb. It is conceptualized that as ethanol is oxidized—oxidation process of ethanol results in the loss of hydrogen. Together with the NaCl split, this is conceived as being a ionophore acting specifically to increase the ion permeability of the cell membrane. Endocytosis should well be disrupted by the Na and/or Cl invaginating the lipid barrier of the cell membrane post viral merging during colonization of the COVID-19 or SARS virus, this increasing, by binding to the host cellular machinery, the mixture/solution now damaging the receptor activity of the spike protein even post cell endocytosis. Perhaps equally by lowering the pH of the alveolar type two cells, the production of surfactant by the mixture/solution theobromine as addition of surfactant is desired and should well be increased by the addition of theobromine as stated herein.

These COVID-19 and CO-SAR viruses, while secondarily impacting airway diameters by reflex inflammation via biochemical cascade from cytokine storms, primarily target critical alveolar capillary membranes thus increasing oxygen diffusion barriers. Sadly, adding semi to full pneumonic processes, which block and tend to decrease oxygen levels, dangerously increases both morbidity and mortality. As in all conditions affecting one's airway diameters, this leads to the impeding of normal required airflow dynamics with associative increased work of breathing. Here however, in COVID-19 and SARs, additional viral damage—the hypoxia (low level of oxygen in blood), is compounded by the effects of alveolar capillary blocking by the damage done by the virus upon the Pneumocyte Type 2 cells. As conceived by the main researcher, this immediately decreases surfactant production levels, causing infiltrates and fibroses to the alveolar clusters that allow gas diffusion of both oxygen and carbon dioxide.

A Major impact of the SARS CoV-2 virus initial entry is via the airways, either directly into the tracheobronchial tree or colonization post nasopharyngeal implantation. It is the airways that are impacted first over a certain time span; mostly in advanced cases—hours. The migration tends down one's airways with colonization of the lungs later, many with pulmonary infiltrates. The surfactant and theobromine are therefore used to cryoprotect the alveolar type 2 cells and their ability to create surfactant. Blocking such needed oxygen diffusion to the cells of the body, i.e., heart, brain, kidneys and causing greater needed airway pressures to open the lungs, such effects present cascades of problems. While the ethanol is utilized to deconstruct, it is also, together with the hypertonic saline, used to directly damage the invading viral envelope.

The usage of the specifically designed mixture solution contains hypertonic saline ranging in percentage strength from 1.8% through and up to 3.7% as hypertonic saline chosen from the range of percentages given herein, said selected percentage of hypertonic saline is dissolved and or placed in 70% through 85% ethanol as solvent (of the selected level of the percentage range chosen of the hypertonic saline) said percentage of the hypertonic saline is selected from the range of hypertonic saline listed herein is placed and dissolved in ethanol, said ethanol percentage strength also composed of a range from 70% strength up to and including 85% ethanol as a solvent. Any percentage within that stated range of ethanol may be selected as mixture solution. Inclusive in said mixture solution is theobromine "$C_7H_8N_4O_2$" said theobromine being dissolved by weight, said theobromine weight dissolved in said solution mixture having a range of weight from 75 milligrams of $C_7H_8N_4O_2$ to 110 milligrams weight. Of these weights available, only a set range from 50 to 90 percentage of such weights stated of the range of theobromine stated weights are selected to be dissolved and or placed in the hypertonic saline and ethanol from the ranges stated are chosen. The percentage of hypertonic saline and the percentage of ethanol and the weight chosen, the percentage of $C_7H_8N_4O_2$, are choices made by the clinical doctor or practitioner depending upon the patient's presenting symptoms and clinical status at the time, the above mixture solution amounts and percentages given above are selected for inhalation only. A differing-composition of theobromine is used as a venous infusion via the individual/s venous route as an "I.V." of theobromine. The selected, chosen mixture solution as stated above is first given being nebulized. Theobromine infusion via venous route as i.v. is administered. The venous route of theobromine given is the same percentages stated that such theobromine to be dissolved and or placed in said mixture solution is composed of a range of percentages from a low of 50% through and up to 90% as a available range of theobromine of the chosen selected weights of the theobromine to be dissolved and or placed in ethanol and the hypertonic saline. As such the $C_7H_8N_4O_2$ dissolved is from 450 mg through and up to 650 mg weight in hypertonic saline which in the intravenous infusion is another range being from 1.8% to a maximum of hypertonic saline of 2.2%. Also, both the $C_7H_8N_4O_2$ selected weight and its selected percentage and the hypertonic saline percentage selected is placed within the chosen percentage of ethanol given. The theobromine, hypertonic saline in selected inclusive of 110 milliliter's volume all dissolved and or placed into one and one-half ethanol percentage is conceived as total volume ranging from 50 milliliters up to a liter of a dextrose and/or water and/or dextrose saline and/or a saline water solution, once or twice in a twenty-four hour period. This alternates with an artificial and/or human surfactant approved for inhalation given either concurrently with the intravenous route or separately. For advanced COVID-19, SARS patients, the inhalation by nebulizer alternating with the stated I.V. solution mixture alternating with the replacement surfactant is conceptionally used for individuals more symptomatic and clinically distressed.

REFERENCES

1. Pathogenesis of COVID-19 from a cell biology perspective. Robert J. Mason. European Respiratory Journal 2020 55:2000607, DOI 10.1183/13993003 00607-2-2020.
2. Choi O. H., Shamim M. T., Padgett W. L., Daly J. W. (1988). "Caffeine and theophylline analogues, Adenosine receptor antagonist and as phosphodiesterase inhibitors." Life Sci 43, 387-398.

The invention claimed is:

1. A method of treating severe acute respiratory syndrome (SARS) or COVID-19 viral infectious disease in the lung of a patient, said method comprising administering to the patient in need thereof a solution comprising an effective proportion of active ingredients consisting of (a) a volume of 1.8 to 3.7% (w/v) hypertonic saline, (b) 37.5 to 110 mg theobromine, and (c) a volume of 70 to 85% (v/v) ethanol, said solution is administered via a nebulizer that generates aerosol particles below 3 microns with a carrier stream of oxygen-enriched air having a density of below 1.28 or 1.30 grams per liter.

2. The method of claim 1, wherein the carrier stream of the nebulizer comprises 25% oxygen mixed with 30% helium.

3. The method of claim 1, wherein the patient is administered 37.5 to 99 mg of theobromine.

4. The method of claim 1, further comprising administering by nebulizer, a pulmonary surfactant as replacement treatment, wherein there is a delay of one to two hours before administering the pulmonary surfactant.

5. A method of treating SARS or COVID19 viral infectious disease in the lung of a patient, said method comprising: administering to the patient in need thereof a solution comprising an effective proportion of active ingredients consisting of a volume of 1.8 to 3.7% (w/v) hypertonic saline and a volume of 70 to 85% (v/v) ethanol, said solution is administered via a nebulizer that generates aerosol particles below 3 microns with a carrier stream of oxygen-enriched air having a density of below 1.28 or 1.30 grams per liter, followed by intravenous infusion of a theobromine solution comprising an effective proportion of (a) 225 to 585 mg theobromine, (b) a volume of 1.8 to 2.2% (w/v) hypertonic saline, optionally with added dextrose, and (c) a volume of 70 to 85% (v/v) ethanol, wherein an artificial or human surfactant is further administered via nebulizer, either concurrently or separately with the theobromine solution.

6. The method of claim 5, wherein said intravenous administration occurs once or twice in a twenty-four hour period.

* * * * *